United States Patent [19]

Heidenreich et al.

[11] Patent Number: 4,988,616
[45] Date of Patent: Jan. 29, 1991

[54] METHOD FOR DETECTING HYDROGEN PEROXIDE EMPLOYING TRIARYL- AND TRIHETARYLMETHANE DERIVATIVES AS REDOX INDICATORS

[75] Inventors: Holger Heidenreich, Cologne; Gerhard Wolfrum, Leverkusen; Klaus Wehling, Wuppertal; Herbert Hugl, Bergisch Gladbach, all of Fed. Rep. of Germany

[73] Assignee: Bayer Aktiengesellschaft, Leverkusen, Fed. Rep. of Germany

[21] Appl. No.: 302,072

[22] Filed: Jan. 24, 1989

Related U.S. Application Data

[63] Continuation of Ser. No. 53,301, May 22, 1987, abandoned.

[30] Foreign Application Priority Data

Jun. 10, 1986 [DE] Fed. Rep. of Germany ....... 3619436

[51] Int. Cl.[5] .................. C12Q 1/00; G01N 21/78
[52] U.S. Cl. .......................................... 435/4; 435/10; 435/11; 435/14; 435/28; 436/66; 436/135; 436/904
[58] Field of Search ............... 436/34, 66, 119, 106, 436/109, 79, 84, 120, 124, 125, 128, 129, 135, 164, 169, 170, 904; 435/4, 7, 10, 11, 14, 28

[56] References Cited

U.S. PATENT DOCUMENTS

| 4,407,960 | 10/1983 | Tratnyek | 422/56 X |
| 4,613,465 | 9/1986 | Yamanishi et al. | 436/135 X |
| 4,670,385 | 6/1987 | Babb et al. | 422/56 X |
| 4,673,635 | 6/1987 | Yamanishi et al. | 436/904 X |

FOREIGN PATENT DOCUMENTS

| 0108382 | 5/1984 | European Pat. Off. | |
| 0110682 | 6/1984 | European Pat. Off. | |
| 0141962 | 5/1985 | European Pat. Off. | |
| 0206316 | 12/1986 | European Pat. Off. | 435/28 |
| 0031641 | 3/1981 | Japan | 436/135 |

OTHER PUBLICATIONS

Hallas et al., J. Chem. Soc., Perkin Trans. 2, (4), pp. 450–456, 1977.

Primary Examiner—Robert J. Hill, Jr.
Attorney, Agent, or Firm—Sprung Horn Kramer & Woods

[57] ABSTRACT

A method for detecting hydrogen peroxide wherein a sample is contacted with a peroxidase or a peroxidatively-active substance and a redox indicator of the following

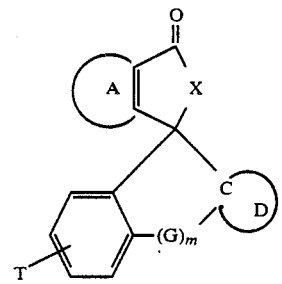

in which A and D independently of one another represent phenyl, pyridyl or imidazolyl,
G represents O, $CH_2$ or S,
m represents the number zero or one, and
X represents O,

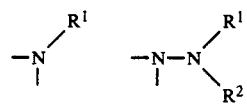

or $-NR^1-NR^2-$ $R^1$ and $R^2$, independently of one another, denote hydrogen, alkyl, cycloalkyl, aryl or aralkyl, or $-NR^1R^2$ together represent a pyrrolidine, pyrazoline, piperidine, piperazine or morpholine radical and (Abstract continued on next page.)

T denotes hydrogen, hydroxyl, alkyl, aryl, alkoxy, phenoxy, SO₃H, —COOH or
whereby a color change is brought out if hydrogen peroxide is present.
7 Claims, 1 Drawing Sheet

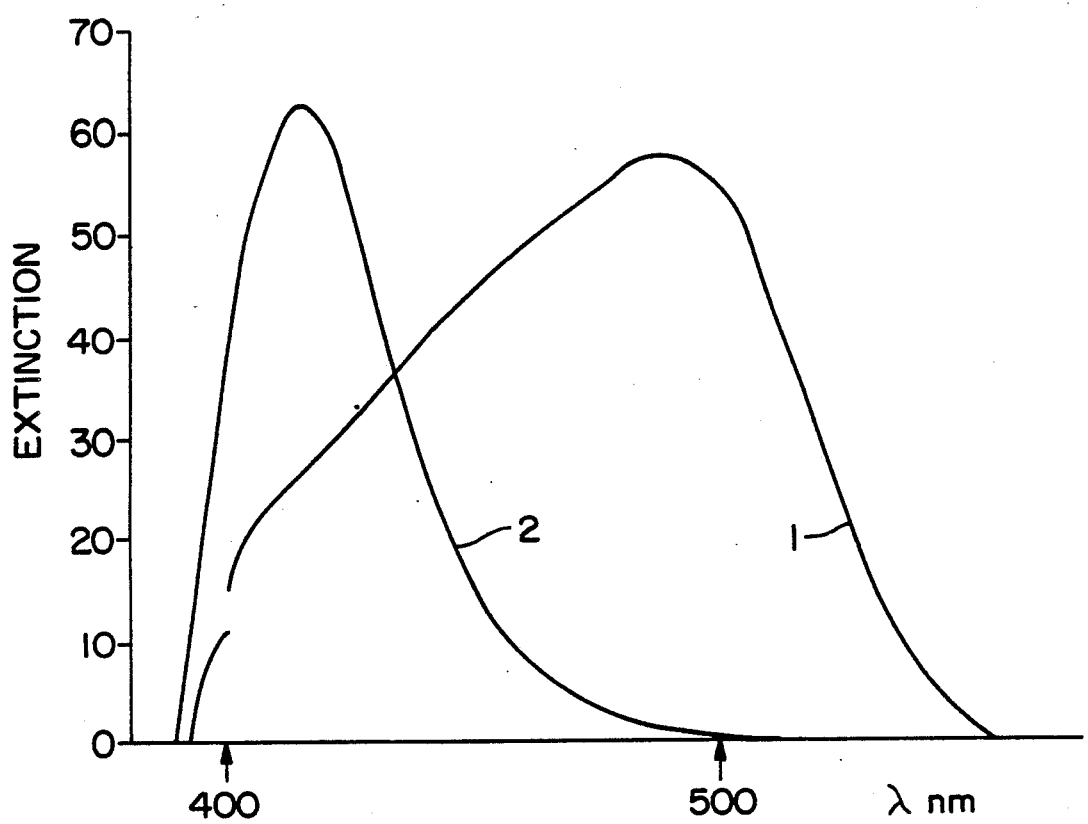

METHOD FOR DETECTING HYDROGEN PEROXIDE EMPLOYING TRIARYL- AND TRIHETARYLMETHANE DERIVATIVES AS REDOX INDICATORS

This application is a continuation of application Ser. No. 053,301, filed 5/22/87, now abandoned.

BACKGROUND OF THE INVENTION

The present invention relates to agents, for detecting redox reactions, containing triaryl- and trihetarylmethane derivatives as redox indicators. These redox indicators can be employed to very good effect for the detection of hydrogen peroxide, particularly with the aid of peroxidases or peroxidatively-active substances These redox indicators are furthermore suitable for the detection of peroxidases or peroxidatively-active compounds, where other peroxides may also be employed as oxidants.

Hydrogen peroxide is a reaction product which is produced during the enzymatically catalyzed oxidation of substrates such as, for example, glucose, cholesterol, uric acid, glycerol, glycerol phosphate, galactose, pyruvate or sarcosine by means of an appropriate oxidase such as glucose oxidase, cholesterol oxidase, uricase, glycerol oxidase, glycerol phosphate oxidase, galactose oxidase, pyruvate oxidase or sarcosine oxidase. The substrates mentioned belong to the group of analytical substances which play a role in clinical/chemical analysis. The hydrogen peroxide formed during the oxidase reaction can be detected polarographically, titrimetrically or potentiometrically. The colorimetric determination of hydrogen peroxide has considerably increased in importance due to the discovery of enzymes, such as peroxidase, catalase or haemoglobin, which convert hydrogen peroxide. Peroxidases, and also peroxidatively active substances (for example haemoglobin and methaemoglobin) catalyze the hydrogen peroxide-dependent oxidation of indicators such as guaiacol, dianisidine hydrochloride or ABTS into colored compounds. One of the best known detection reactions for hydrogen peroxide is the so-called "Trinder reaction" (Trinder, P. Ann. Clin Biochem., volume 6 (1969), pp. 24–27). 4-amino-antipyrine is oxidized by hydrogen peroxide in the presence of a peroxidase. The oxidation product is capable of coupling with a phenol or phenol derivative, a usually red quinone imine dyestuff being produced the concentration of which may be determined photometrically.

SUMMARY OF THE INVENTION

The present invention relates to agents, for the detection of redox reactions, containing compounds of the general formula I

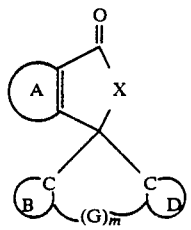

(I)

in which

A, B and D, independently of one another, represent the radical of an aromatic or heteroaromatic compound, G represents O, $CH_2$ or S, m represents the number 0 or 1, and X represents O,

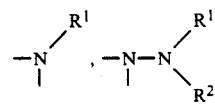

or $-NR^1-NR^2-$, where aromatic radicals are the aryl or naphthyl radicals, and heteroaromatic radicals are the pyridyl, imidazolyl, pyrazinyl and indolyl radicals, which themselves may carry substituents which are conventional in dyestuff chemistry, $R^1$ and $R^2$, independently of one another, denote hydrogen, alkyl, cycloalkyl, aryl or aralkyl which may be substituted by substituents which are conventional in dyestuff chemistry, or $-NR^1R^2$ represents a pyrrolidine, pyrazoline, piperidine, piperazine or morpholine radical which may be substituted by substituents which are conventional in dyestuff chemistry, as redox indicators.

BRIEF DESCRIPTION OF THE DRAWING

The drawing is a graph of extinction vs. λnm. Curve 1 depicts the absorption spectrum at pH 6.57 and curve 2 depicts the absorption spectrum at pH 4.6.

DETAILED DESCRIPTION OF THE INVENTION

Substituents which are conventional in dyestuff chemistry are, for example, halogen, hydroxyl, alkoxy, aryloxy, aralkoxy, aryl, cycloalkyl, hetaryl, alkylmercapto, arylmercapto, alkylsulphonyl, cyano, alkylcarbonyl, alkylcarbonyloxy, nitro, acylamino, alkylsulphonic acid, arylsulphonic acid, alkylcarboxylic acid, aralkylcarboxylic acid, amino which may be substituted by 1 or 2 alkyl, aryl or aralkyl groups which themselves may again be substituted by halogen, cyano, hydroxyl, sulphonic acid, carboxylic acid or substituted amino, or amino groups the substituents of which are cyclized.

Alkyl preferably represents $C_1-C_{22}$-alkyl, particularly $C_1-C_{12}$-alkyl, and very particularly $C_1-C_6$-alkyl, and alkenyl preferably represents $C_2-C_5$-alkenyl.

Halogen is taken to mean, in particular, fluorine, chlorine and bromine.

In particular, cycloalkyl is taken to mean cyclopentyl and cyclohexyl, aryl is taken to mean phenyl and naphthyl, aralkyl is taken to mean benzyl and phenethyl, and hetaryl is taken to mean pyridyl, pyrimidyl, pyrazinyl, triazinyl, imidazolyl, oxazolyl or thiazolyl.

Acyl is preferably $C_1$- to $C_4$-alkylcarbonyl and -sulphonyl and benzoyl.

The compounds of the general formula (I) are widely known as color formers, for example for copying paper or thermal printing paper (EP-A 108,382, EP-A 141,962). In the case of copying paper, the color formers are present in encapsulated form. During writing, the capsules are broken and the color formation by the liberated color formers occurs on contact with acid-modified aluminas.

Surprisingly, it has now been determined that compounds of the general formula (I) are also very well suited as redox indicators. These compounds are particularly well suited as indicators for the qualitative or quantitative detection of hydrogen peroxide or also for the detection of peroxidases or peroxidatively-active substances. The oxidation of the indicators by the hydrogen peroxide or another peroxide (for example cumenyl hydroperoxide, strontium peroxide, 2,5-dimethylhexane 2,5-dihydroperoxide or diisopropylbenzoyl hydroperoxide) can occur due to the catalytic action of a peroxidase or a peroxidatively-active substance. Suitable peroxidases are those from horseradish or potatoes or those of microbiological origin. Peroxidatively-active substances are taken to mean those substances which catalyze the transfer of the redox equivalents from hydrogen peroxide or another peroxide onto the indicators, such as, for example, haemoglobin, methaemoglobin or myoglobin. Furthermore, the compounds of the general formula (I) are suitable for determining oxidants, such as, for example, persulphate, peracetate, chloramine T or cyanoferrate complexes such as potassium hexacyanoferrate.

The compounds of the general formula (I) can be particularly successfully employed in test agents for substrates such as, for example, glucose, cholesterol, uric acid, glycerol, glycerol phosphate, galactose, pyruvate or sarcosine which are oxidized by an appropriate oxidase such as glucose oxidase, cholesterol oxidase, uricase, glycerol oxidase, glycerol-phosphate oxidase, galactose oxidase, pyruvate oxidase or sarcosine oxidase in the presence of oxygen with formation of hydrogen peroxide. The hydrogen peroxide formed is detected using the compounds of the general formula (I).

As already discussed, the compounds of the general formula (I) are also suitable for the detection of peroxidases or peroxidatively-active substances. Test systems which may be mentioned here are the detection of occult blood or peroxidase-labelled immune tests.

In the context of the present invention, test agents or test systems are taken to mean, for example, those which can be measured in a cell. The test agents contain, besides the redox indicators of the general formula (I), all those reagents, such as enzymes, substrates, coenzymes, effectors, antigens, antibodies etc., which are necessary for the determination of the particular parameter. In addition, these test agents can also contain non-reacting substances, such as, for example, buffers, wetting agents and stabilizers. Reagent combination$, which are present as a solution, as a mixture of powders, as tablets or as a lyophylizate, may be prepared from the reagents and substances mentioned. The reagent combination (if not already present as a solution) is taken up in water or another suitable solvent and made up into a reagent solution. If the reagent combination comprises individual components, these should be mixed with one another. After mixing the sample (for example substrate solution, enzyme solution, blood, serum, plasma or urine) with an aliquot of the reagent mixture, the resultant color is measured on a photometer and the respective concentration or substrate concentration is calculated via the molar extinction coefficients and the volumes of reagent or sample added. Both kinetic and end-point measurements are possible.

The compounds of the general formula (I), together with peroxidase or a peroxidatively-active substance, the reagents or other enzymes which are necessary for the determination of the particular parameter, the buffer system, if appropriate wetting agents and activators, and also other adjuvants, may also be impregnated onto absorptive reagent supports such as papers, fleeces, etc. For this purpose, one or more impregnation solutions may be prepared in the form of aqueous or organic or mixed solutions, depending on how the reagents or adjuvants dissolve. Absorptive or swellable supports, preferably filter paper or absorptive glass or plastic fleeces, are impregnated or sprayed with these solutions. The supports are subsequently dried. The reagent supports thus prepared can be employed as rapid diagnostic agents for the direct determination of the contents of liquids (for example in body liquids such as blood, urine or saliva, or in foods, for example fruit juices, milk or others). During this, the liquid is applied directly onto the reagent support or the latter is dipped briefly in the liquid. Semi-quantitative determination is possible by allocating the color produced to a comparison color. Quantitative evaluation can be carried out by remission photometry. In this, the fact that dyestuffs which have their absorption maximum in the long-wave region of the spectrum are usually developed from the compounds of the formula (I) has an advantageous effect. Light diodes can then be used as the light source for the measurement of such dyestuffs.

It is also possible to introduce the compounds of the general formula (I) into support matrices which have been prepared from casting solutions. Examples which may be mentioned here are cellulose, cellulose derivatives, gelatins, gelatin derivatives or also plastics such as polyurethanes and acrylamide. It is advantageous here for the compounds of the general formula (I) and, if appropriate, the other necessary reagents to be added directly to the casting solution, it thereby becoming possible for the test device, comprising support and reagents, to be prepared in one step.

A reagent solution with which the substrates or enzymes described above can be determined in the cell on a photometer may be prepared by eluting the above-mentioned reagents from the absorptive support using water or buffer or serum.

Suitable buffers for the test agents mentioned are phosphate, citrate, borate or GOOD buffers having alkali metal or ammonium counterions. However, other systems are likewise practicable. A pH of 6 to 10, particularly 6.5 to 7.5, should be aimed at.

Wetting agents are, in particular, anionic and cationic wetting agents which interact ionically with the zwitterionic compounds according to the invention. However, non-ionogenic wetting agents which activate the enzymes are likewise practicable. Sodium lauryl sulphate, dioctyl sodium sulfosuccinate and alkylaryl polyether alcohols are preferred.

The known effectors for the particular enzymatic reaction should be employed as effectors.

Conventional thickeners, solubilizers, emulsifiers, optical brighteners, contrasting agents, etc., as are known in corresponding tests with other chromogens, may be appropriate as other adjuvants.

Of the compounds of the formula (I), the compounds of the formula (II)

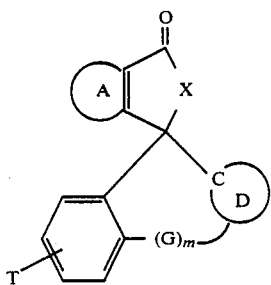

in which
  A denotes optionally substituted phenyl, pyridyl or imidazolyl,
  T denotes hydrogen, hydroxyl, alkyl, aryl, alkoxy, phenoxy, SO$_3$H, —COOH or

where R$^1$ and R$^2$ have the abovementioned meaning, and X, G, D and m have the abovementioned meaning, are preferred.

Compounds of the formula (III)

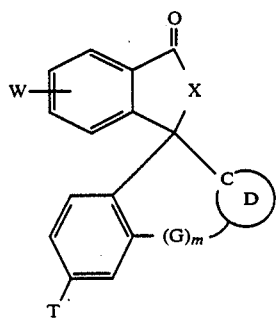

in which
  W denotes hydrogen,

alkyl, alkoxy or halogen,
  T denotes hydrogen, alkyl, alkoxy or

X denotes

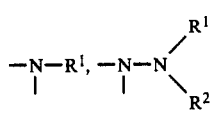

or —NH—NR$^1$—,

D denotes the radical phenyl, naphthyl or indolyl, and
  G, R$^1$, R$^2$ and m have the abovementioned meaning,
are of particular interest.

Very particularly preferred compounds are those of the formula (IV)

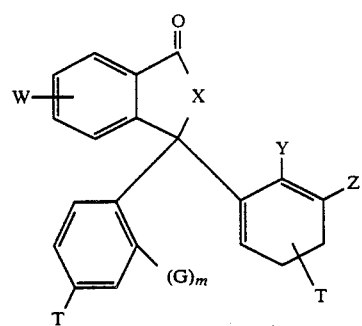

in which
  X denotes

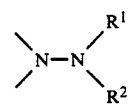

or —NH—NR$^1$,
  W denotes hydrogen or

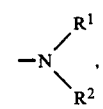

T denotes hydrogen, C$_1$-C$_4$-alkyl, C$_1$-C$_4$-alkoxy or

G denotes O,
m denotes 0 or 1, and
Y and Z denote hydrogen or a fused benzo ring, and
R$^1$ and R$^2$, independently of one another, denote hydrogen, C$_1$-C$_4$-alkyl which may be substituted by halogen, hydroxyl, cyano, C$_1$-C$_5$-alkoxycarbonyl, —SO$_3$H or —COOH, or denote aryl or aralkyl, or
NR$^1$R$^2$ denotes a pyrrolidine, piperidine or morpholine radical.

Very particularly preferred compounds are those of the formula (V)

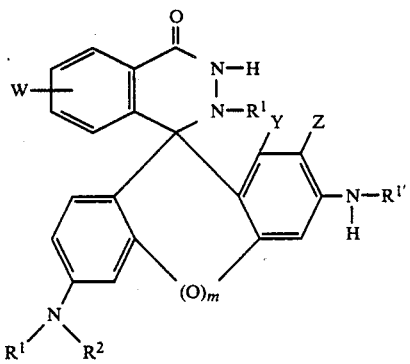

in which

W, R¹, R², Y, Z and m have the abovementioned meaning.

Processes for the preparation of the compounds mentioned are described in EP-A 141,962 and EP-A 108,382.

The present invention is described in greater detail and illustrated by means of the following examples.

EXAMPLE 1

4.15 g of 3,3-bis-(4-dimethylaminophenyl)-6-dimethylamino-phthalide are refluxed in 20 ml of ethanol with 10 ml of hydrazine hydrate. After 3 hours, the reaction batch is discharged into 100 ml of ice-water and filtered under suction. The crude product of the following constitution

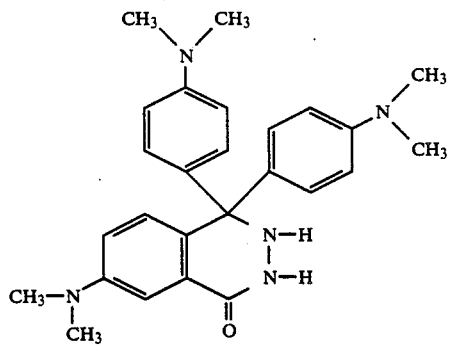

melts at 263° C.

EXAMPLE 2

4.15 g of 3,3-bis-(4-dimethylaminophenyl)-6-dimethylamino-phthalide are heated for 2 hours at 150° C. with 20 ml of diethanolamine. The solution is allowed to cool and discharged into ice-water, and the yellowish precipitate is filtered off under suction. After recrystallization from ethanol, the substance of the follow-constitution

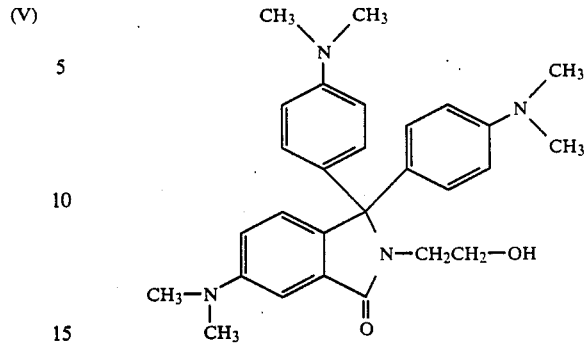

melts at 252° C.

Color of the oxidation product: yellow-orange

EXAMPLE 3

31.8 g of 3,3-bis-(4-hydroxyphenyl)-1(3H)-isobenzofuranone are refluxed in 150 ml of ethanol with 30 ml of hydrazine hydrate. After 5 hours, the mixture is poured onto ice and acidified using acetic acid. The precipitate, after filtering off under suction, is recrystalized from ethanol. The substance, melting at 279° C., has the following formula

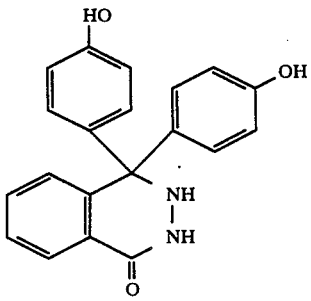

Color of the oxidation product: orange

EXAMPLE 4

15.7 g of 2-(2-hydroxy-4-diethylamino)benzoylbenzoic acid are introduced into 62 ml of sulphuric acid monohydrate at a temperature of 8° to 12° C. 9.95 g of 4-methoxy-diphenylamine are subsequently added and the mixture is stirred for 2 days at room temperature. The reaction solution is then discharged onto ice and adjusted to pH 11 using a sodium hydroxide solution, a layer of 300 ml of toluene is added, and the mixture is refluxed for 3 hours. The toluene phase is subsequently separated off and concentrated by evaporation. After treatment with activated charcoal, the following substance, having the melting point 194° C., crytallizes from toluene.

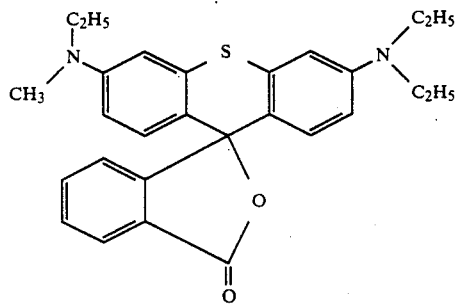

Color of the oxidation product: grey-violet.

EXAMPLE 5

4.62 g of 3-diethylamino-7-anilinofluoroan are refluxed for 1 hour in 25 ml of ethyl glycol with 6 ml of hydrazine hydrate. After cooling, ice-water is added dropwise and the precipitation is filtered off under suction. The compound of the following constitution melts at 146° C.

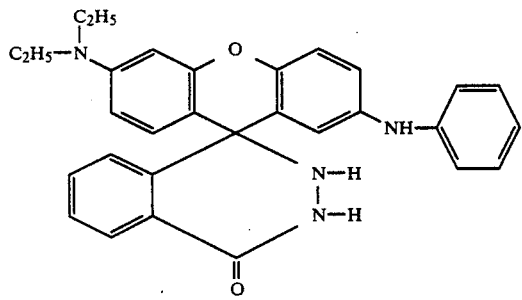

The compounds mentioned below are prepared analogously. *=color of the oxidation product

EXAMPLE 6

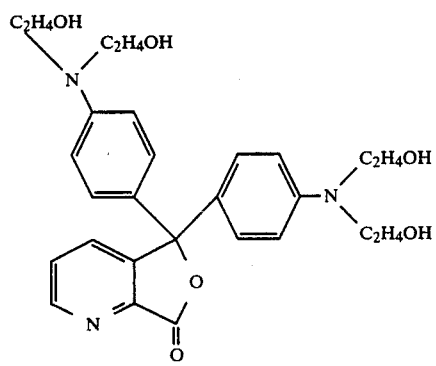

EXAMPLE 7

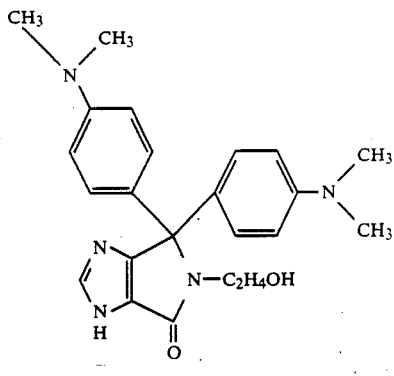

EXAMPLE 8

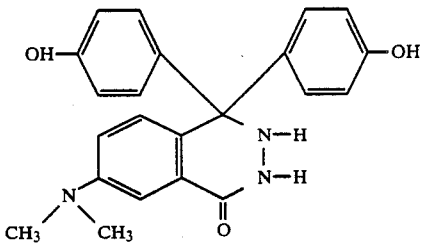

EXAMPLE 9

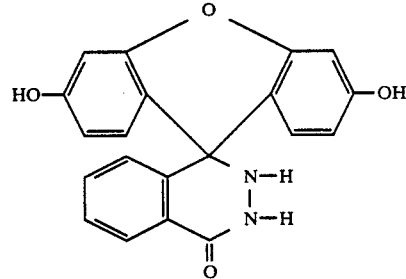

EXAMPLE 10

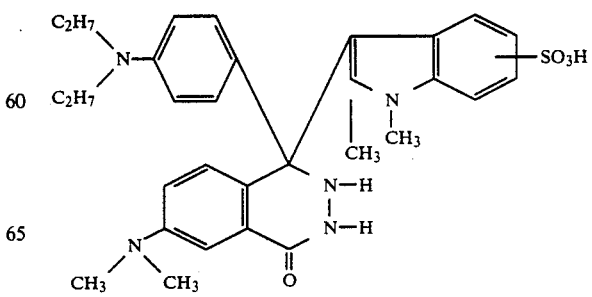

EXAMPLE 11
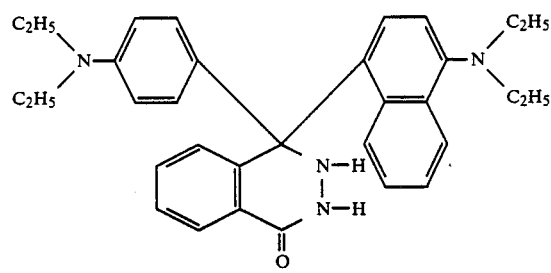
EXAMPLE 12
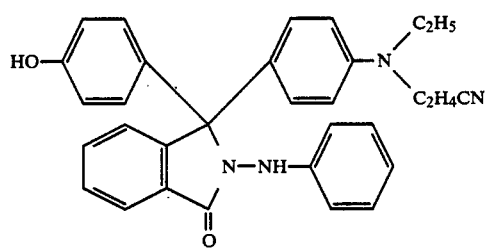
EXAMPLE 13
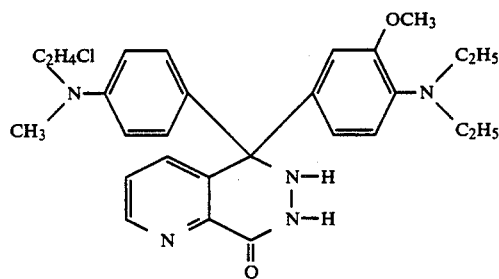
EXAMPLE 14
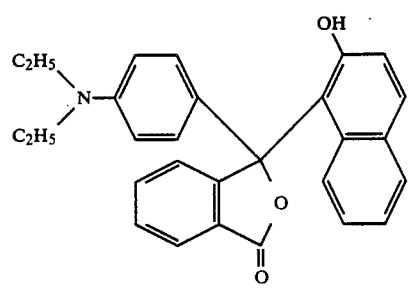
EXAMPLE 15
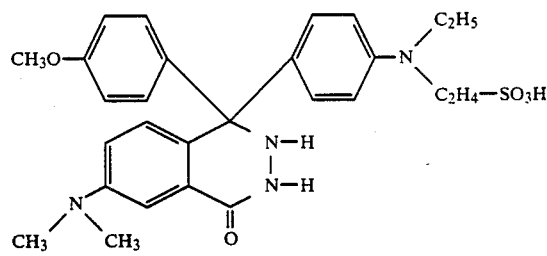
EXAMPLE 16
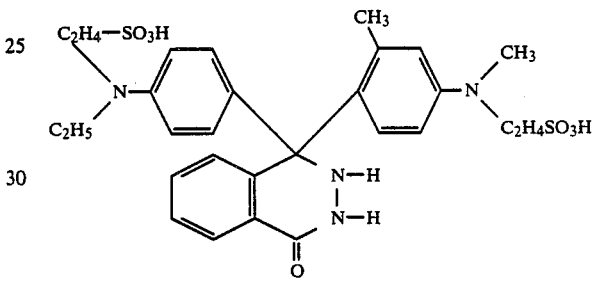
EXAMPLE 17
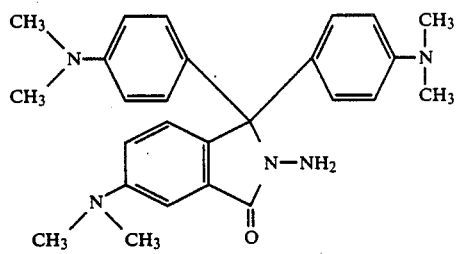
EXAMPLE 18
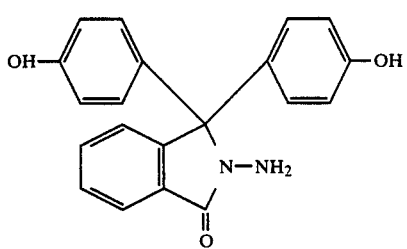

EXAMPLE 19
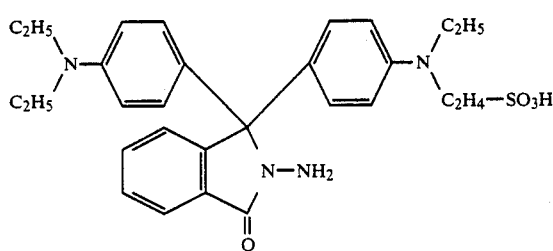
EXAMPLE 20
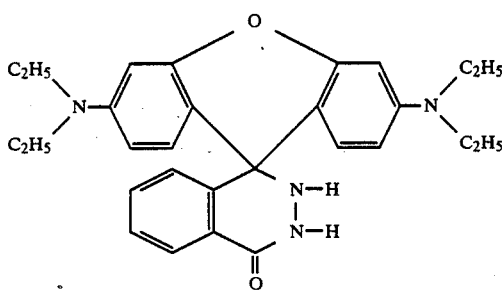
EXAMPLE 21
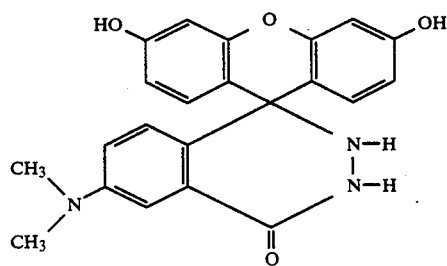
EXAMPLE 22
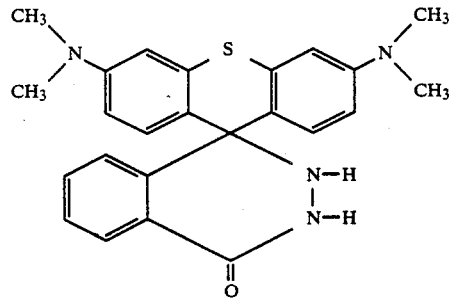
EXAMPLE 23
TABLE 1
| pH | Color | Absorption maximum (nm) | Extinction difference/ 5 minutes |
|---|---|---|---|
| 4.55 | yellow | 415 | 1.707 |
| 6.57 | yellow-orange | 490 | 1.351 |
| 7.80 | yellow-orange | 490 | 1.803 |
EXAMPLE 24
TABLE 2
| | Extinction difference/5 minutes | | | |
|---|---|---|---|---|
| | $H_2O_2$ | Concentration (ext. at 240 nm) | | |
| | 0.021 | 0.045 | 0.083 | 0.168 |
| Compound from Ex. 1 | 0.116 | 0.229 | 0.419 | 0.888 |
| 490 nm | 0.114 | 0.225 | 0.441 | 0.910 |
| DCHBS/aminopy | 0.139 | 0.274 | 0.546 | 1.076 |
| 510 nm | 0.144 | 0.273 | 0.534 | 1.103 |
EXAMPLE 25
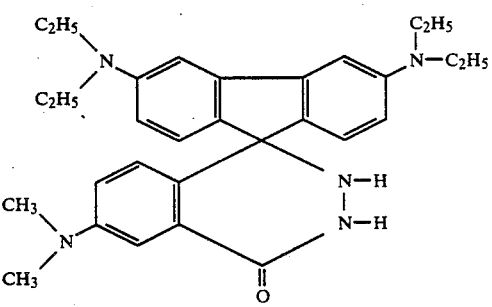
EXAMPLE 26
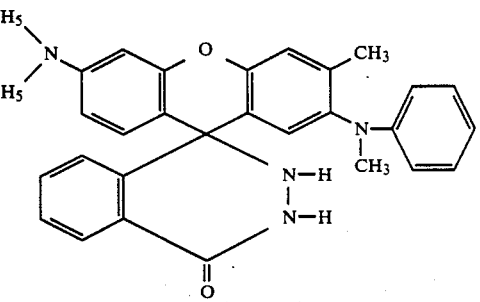
EXAMPLE 27
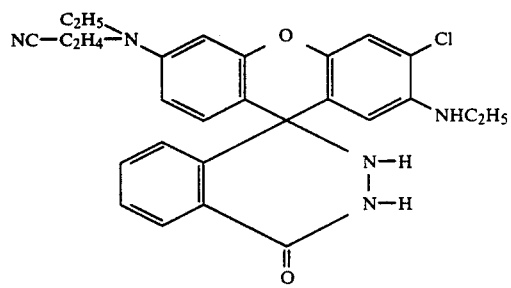

EXAMPLE 28
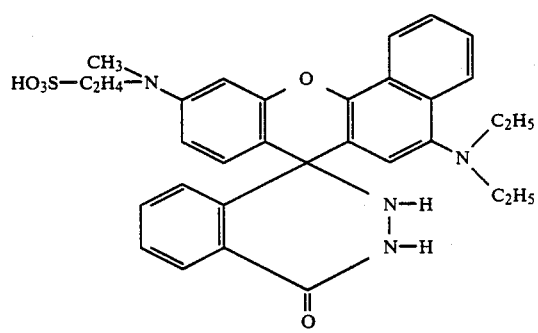
EXAMPLE 29
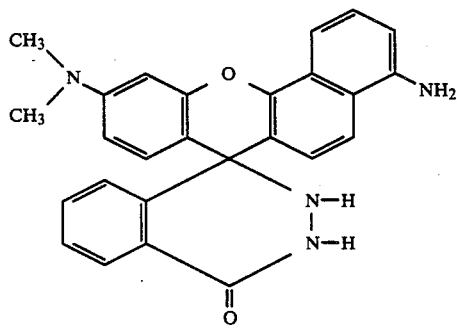
EXAMPLE 30
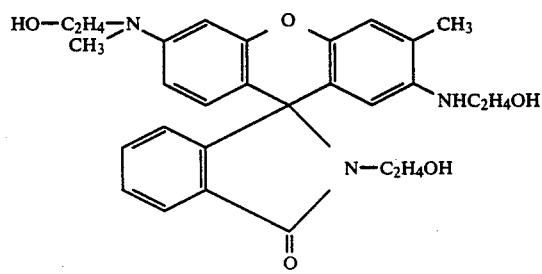
EXAMPLE 31
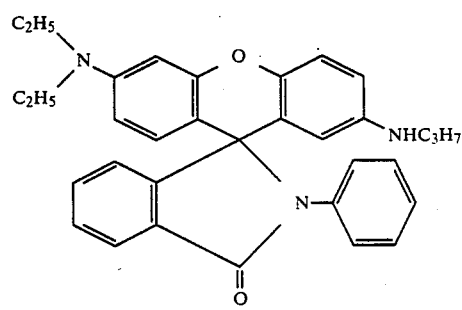
EXAMPLE 32
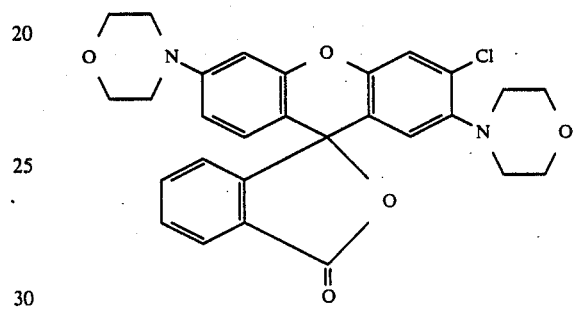
EXAMPLE 33
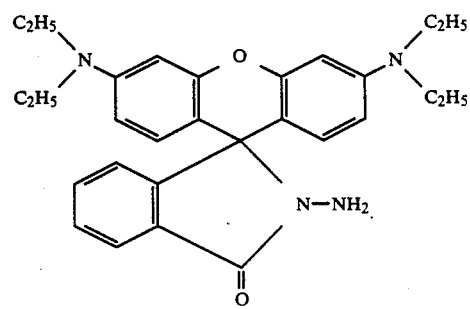
EXAMPLE 34
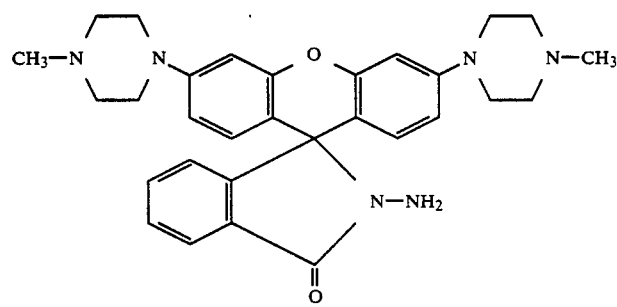

EXAMPLE 35

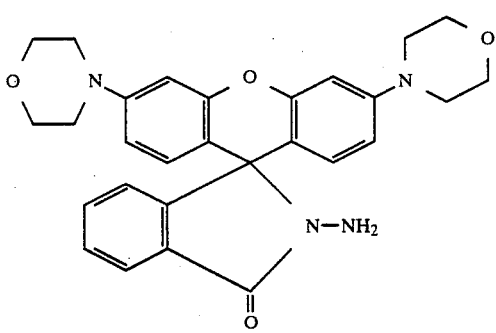

EXAMPLE 36

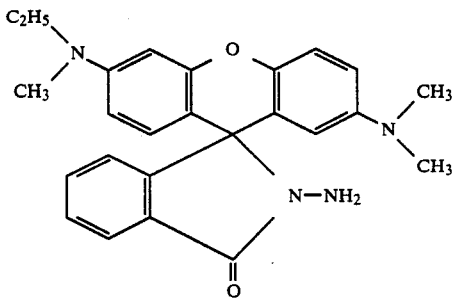

EXAMPLE 37

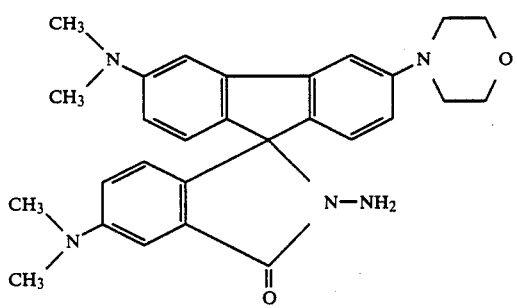

EXAMPLE 38

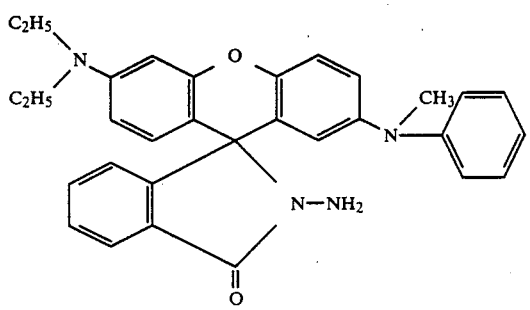

EXAMPLE 39

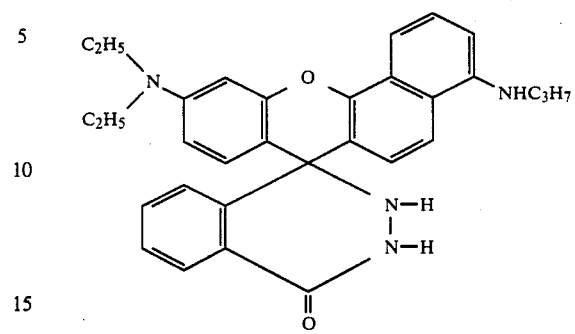

EXAMPLE 40

In order to test the compound of Example 1 as an indicator in an $H_2O_2$/peroxidase test system, this compound was dissolved in DMF to a concentration of 5 mM. This solution was then mixed 1+1 with buffer (citrate 0.1 M/l, pH 4.55, THAM 0.1 M/l, pH 6.57 and pH 7.8, and 5 μl of peroxidase (500 kU/l) were added to 0.5 ml of this solution. After addition of 10 μl of $H_2O_2$ (3.4 mM/l $\hat{=}$ $E_{240}$=0.168) and an incubation time of 5 minutes, the extinctions were measured. As FIG. 1 shows, the absorption maximum shifts depending on the pH.

Curve 1 shows the absorption spectrum at pH 6.57 and curve 2 at pH 4.6.

Table 1 shows the extinctions measured at the different wavelengths and pHs.

TABLE 1

| pH | Color | Absorption maximum (nm) | Extinction difference/ 5 minutes |
|---|---|---|---|
| 4.55 | yellow | 415 | 1.707 |
| 6.57 | yellow-orange | 490 | 1.351 |
| 7.80 | yellow-orange | 490 | 1.803 |

In order to test the function and linearity, 5 μl of peroxidase (500 kU/l) and 5 μl of $H_2O_2$ of different concentration were added to 0.5 ml of the above solution with THAM buffer pH 7.8. Table 2 shows the results compared to the "Trinder color system" 4-aminoantipyrine/dichloro-2-hydroxybenzenesulphonic acid.

TABLE 2

| | Extinction difference/5 minutes | | | |
|---|---|---|---|---|
| | $H_2O_2$ Concentration (ext. at 240 nm) | | | |
| | 0.021 | 0.045 | 0.083 | 0.168 |
| Compound from Ex. 1 490 nm | 0.116 | 0.229 | 0.419 | 0.888 |
| | 0.114 | 0.225 | 0.441 | 0.910 |
| DCHBS/aminopy. 510 nm | 0.139 | 0.274 | 0.546 | 1.076 |
| | 0.144 | 0.273 | 0.534 | 1.103 |

Table 3 shows the results of the test for interferences by ascorbic acid. For this test, 5 μl of an $H_2O_2$ solution ($H_2O_2$ concentration in the sample=$E_{240}$=0.242) and a further 5 μl of an ascorbic acid solution of 1mM/l are added to the above batch and the resulting extinction is measured.

TABLE 3

|  | $E_1$ | $E_2$ | $\Delta E_{490\,nm}$ |
|---|---|---|---|
| without ascorbic acid | 0.694 | 1.963 | 1.269 |
|  | 0.720 | 1.992 | 1.272 |
|  | 0.709 | 2.002 | 1.293 $\bar{x} = 1.278$ |
| with ascorbic acid | 0.585 | 1.899 | 1.314 |
|  | 0.573 | 1.859 | 1.286 |
|  | 0.577 | 1.854 | 1.277 $\bar{x} = 1.292$ |

The values measured in the presence of ascorbic acid are, on average, about 1.1% above the values which were measured in the absence of ascorbic acid. The present test is thus not influenced by ascorbic acid.

EXAMPLE 41

Test of the compound from Example 5 Batch:
1,000 μl of buffer (citrate 0.1 M/l pH 5, THAM 0.1 M/l pH 7 and pH 9)
900 μl of DMF
100 μl of the compounds from Example 5, 2.02 mM in DMF
20 μl of peroxidase (1,000 kU/l)
20 μl of $H_2O_2$ solution The measured absorption maximum is at 720 nm. The extinction differences at different pH values are listed in Table 4. The sample concentration was 5 mM/l with respect to $H_2O_2$.

TABLE 4

|  | $\Delta E_{720}$ after 5 minutes |
|---|---|
| pH 5 | 0.110 |
| pH 7 | 0.185 |
| pH 9 | 0.040 |

The decrease in the extinction within 20 minutes (color stability) is 0.8%. The interference by ascorbic acid was tested analogously to Example 40. Table 5 shows the results.

TABLE 5

|  | $E_1$ | $E_2$ | $\Delta E_{720\,nm}$ |
|---|---|---|---|
| without ascorbic acid | 0.138 | 0.374 | 0.236 |
|  | 0.148 | 0.380 | 0.232 |
|  | 0.140 | 0.375 | 0.235 $\bar{x} = 0.234$ |
| with ascorbic acid | 0.107 | 0.349 | 0.242 |
|  | 0.107 | 0.353 | 0.246 |
|  | 0.103 | 0.358 | 0.255 $\bar{x} = 0.248$ |

In the presence of ascorbic acid, the measured values are, on average, about 5.7% higher.

Table 5 shows the linearity and function test. $H_2O_2$ solutions of different concentrations were added to the above test batch and the extinction was measured after 5 minutes.

TABLE 6

| [$H_2O_2$] sample | Compound Example 5 pH 7  720 nm | | | Comparison 4-AAP/DCHBS (Trinder) pH 7.5  510 nm | | |
|---|---|---|---|---|---|---|
| $E_{240}$ | $E_1$ | $E_2$ | $\Delta E_{720}$ | $E_1$ | $E_2$ | $\Delta E_{510}$ |
| 0.072 | 0.146 | 0.204 | 0.058 | 0.010 | 0.321 | 0.311 |
| 0.099 | 0.139 | 0.248 | 0.109 | 11 | 0.714 | 0.703 |
| 0.151 | 0.139 | 0.275 | 0.136 | 10 | 1.040 | 1.030 |
| 0.200 | 0.140 | 0.333 | 0.193 | 15 | 1.402 | 1.387 |
| 0.258 | 0.148 | 0.371 | 0.223 | 10 | 1.703 | 1.693 |
| 0.303 | 0.139 | 0.400 | 0.261 | 11 | 1.976 | 1.965 |
| 0.371 | 0.138 | 0.418 | 0.280 | 12 | 2.270 | 2.258 |
| 0.413 | 0.139 | 0.432 | 0.293 | 12 | 2.405 | 2.393 |
| 0.460 | 0.148 | 0.440 | 0.292 | 11 | 2.678 | 2.667 |

TABLE 6-continued

| [$H_2O_2$] sample | Compound Example 5 pH 7  720 nm | | | Comparison 4-AAP/DCHBS (Trinder) pH 7.5  510 nm | | |
|---|---|---|---|---|---|---|
| $E_{240}$ | $E_1$ | $E_2$ | $\Delta E_{720}$ | $E_1$ | $E_2$ | $\Delta E_{510}$ |
| 0.512 | 0.139 | 0.443 | 0.304 | 10 | 2.771 | 2.781 |

It is understood that the specification and examples are illustrative but not limitative of the present invention and that other embodiments within the spirit and scope of the invention will suggest themselves to those skilled in the art.

We claim:
1. A method for detecting hydrogen peroxide comprising contacting a sample with a peroxidase or a peroxidatively-active substance and a reflux indicator of the formula

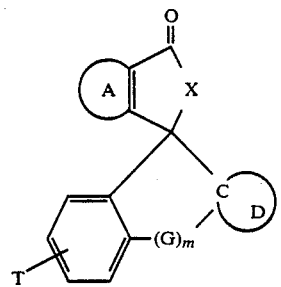

in which

A and D, independently of one another represent unsubstituted phenyl, pyridyl or imidazolyl or phenyl, pyridyl, or imidazolyl substituted by halogen, hydroxyl, alkoxy, aryloxy, aralkoxy, aryl, cycloalkyl, hetaryl, alkylmercapto, arylmercapto, alkylsulphonyl, cyano, alkylcarbonyl, alkylcarbonyloxy, nitro, acylamino, alkylsulphonic acid, arylsulphonic acid, alkylcarboxylic acid, aralkylcarboxylic acid, amino which is unsubstituted or substituted by 1 or 2 alkyl, aryl or aralkyl groups, which themselves are unsubstituted or substituted by halogen, cyano, hydroxyl, sulphonic acid, carboxylic acid or substituted amino, or amino groups, the substituents of which are cyclized, G represents O, $CH_2$ or S, m represents the number zero or one, X represents

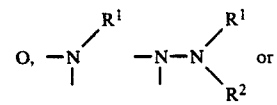

—$NR^1$—$NR^2$—, $R^1$ and $R^2$ denote hydrogen and

T denotes hydrogen, hydroxyl, alkyl, aryl, alkoxy, phenoxy, $SO_3H$, —COOH or

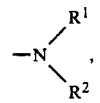

whereby a color change is brought about if hydrogen peroxide is present and detecting any color change in the sample.

2. The method according to claim 1, wherein the redox indicator is of the formula

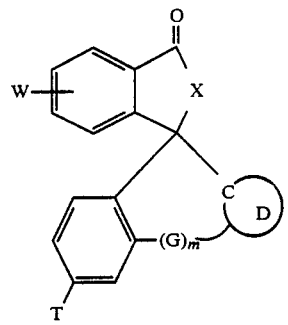

in which
W denotes hydrogen,

alkyl, alkoxy or halogen,
T denotes hydrogen, alkyl, alkoxy or

and
D denotes the radical phenyl, naphthyl or indolyl.

3. A method according to claim 1, wherein the redox indicator is of the formula

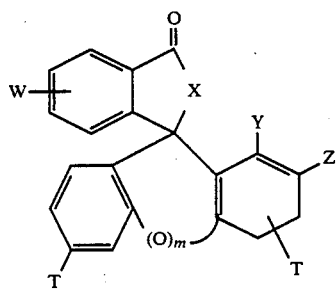

in which
W denotes hydrogen or

T denotes hydrogen, $C_1$-$C_4$-alkyl, $C_1$-$C_4$-alkoxy or

m denotes 0 or 1, and

Y and Z denote hydrogen or a fused benzo ring, and
$R^1$ and $R^2$, independently of one another, denote hydrogen, $C_1$-$C_4$-alkyl which may be substituted by halogen, hydroxyl cyano, $C_1$-$C_5$-alkoxycarbonyl, —$SO_3H$ or —COOH, or denote aryl or aralkyl, or
$NR^1R^2$ denotes a pyrrolidine, piperidine or morpholine radical.

4. The method according to claim 3, wherein the redox indicator is of the formula

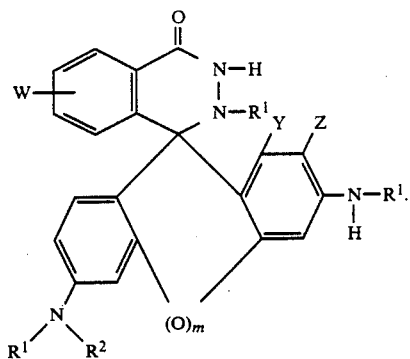

5. The method according to claim 1, wherein the redox indicator is

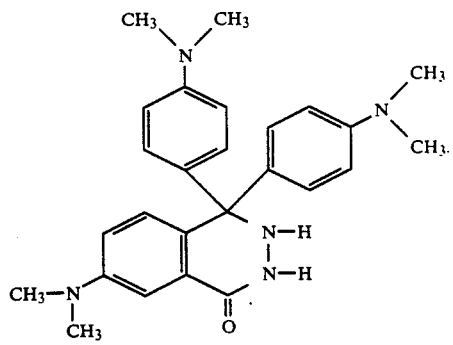

6. The method according to claim 1, wherein the redox indicator is

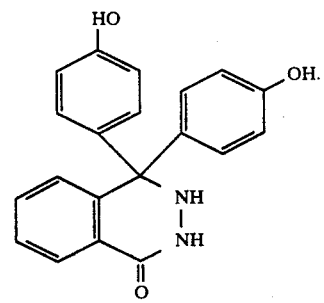

7. A method for detecting one or more of glucose, cholesterol, uric acid, glycerol, glycerol phosphate, galactose, pyruvate or sarcosine comprising conducting oxidation in the presence of oxygen and a corresponding oxidase selected from the group consisting of glucose oxidase, cholesterol oxidase, uricase, glycerol oxidase, glycerol-phosphate oxidase, galactose oxidase, pyruvate oxidate and sarcosine oxidase and detecting for a resultant formation of hydrogen peroxide by employing the method according to claim 1.

* * * * *

UNITED STATES PATENT AND TRADEMARK OFFICE
CERTIFICATE OF CORRECTION

PATENT NO. : 4,988,616

DATED : January 29, 1991

INVENTOR(S) : Heidenreich et al.

It is certified that error appears in the above-identified patent and that said Letters Patent is hereby corrected as shown below:

Column 20:

Claim 1, line 3,   Delete " reflux " and substitute -- redox --

Col. 20, line 55   Delete

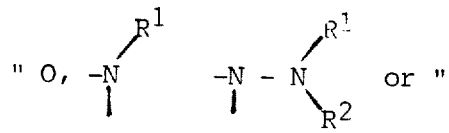

" O,                  or "

Column 21:

Claim 3, line 1,   Delete " A " and substitute -- The --

Signed and Sealed this

Twenty-fifth Day of May, 1993

Attest:

MICHAEL K. KIRK

*Attesting Officer*        *Acting Commissioner of Patents and Trademarks*